United States Patent
Wiksell et al.

(10) Patent No.: US 8,323,210 B2
(45) Date of Patent: Dec. 4, 2012

(54) FINE NEEDLE ARRANGEMENT FOR CELL SAMPLING

(75) Inventors: Hans Wiksell, Taby (SE); Vilhelm Ekstrand, Nacka (SE); Gert Auer, Solna (SE)

(73) Assignee: NeoDynamics AB, Lidingo (SE)

( * ) Notice: Subject to any disclaimer, the term of this patent is extended or adjusted under 35 U.S.C. 154(b) by 457 days.

(21) Appl. No.: 12/601,074

(22) PCT Filed: May 20, 2008

(86) PCT No.: PCT/EP2008/056141
§ 371 (c)(1),
(2), (4) Date: Nov. 20, 2009

(87) PCT Pub. No.: WO2008/142060
PCT Pub. Date: Nov. 27, 2008

(65) Prior Publication Data
US 2010/0160828 A1    Jun. 24, 2010

(30) Foreign Application Priority Data

May 21, 2007 (EP) .................................. 07108566

(51) Int. Cl.
*A61B 10/00* (2006.01)
(52) U.S. Cl. ........................................... 600/562
(58) Field of Classification Search ........... 600/562–572
See application file for complete search history.

(56) References Cited

U.S. PATENT DOCUMENTS

| | | | |
|---|---|---|---|
| 4,713,061 A | 12/1987 | Tarello et al. | |
| 5,330,443 A | 7/1994 | Powles et al. | |
| 5,573,008 A * | 11/1996 | Robinson et al. | 600/567 |
| 2002/0055715 A1 | 5/2002 | Young et al. | |

FOREIGN PATENT DOCUMENTS

| WO | 96/32146 | 10/1996 |
|---|---|---|
| WO | 99/13928 | 3/1999 |
| WO | 2006007090 A2 | 1/2006 |
| WO | 2006/036108 | 4/2006 |
| WO | 2006/036112 | 4/2006 |

OTHER PUBLICATIONS

International Search Report dated Dec. 12, 2008, from corresponding PCT application.
Office Action, Issued Mar. 30, 2011, in Application No. 200880025390.

\* cited by examiner

*Primary Examiner* — Jeffrey G Hoekstra
(74) *Attorney, Agent, or Firm* — Young & Thompson

(57) ABSTRACT

Fine needle arrangement for taking a sample of cells from suspicious lesions by using fine needle aspiration (FNA) technique, including a tubular needle member (1), a storage compartment (2) enclosing a chamber, and a coupling (3) to which a connector may be attached. The chamber is configured with a gradually increasing cross-sectional area from the distal part of the chamber to the proximal part of the chamber, such that the chamber has no residual spaces where cell samples may be trapped, and that an efficient air streaming is achieved.

8 Claims, 5 Drawing Sheets

FINE NEEDLE ARRANGEMENT FOR CELL SAMPLING

TECHNICAL FIELD

The present invention relates to a needle arrangement for taking a sample of cells from suspicious lesions with a so called fine needle aspiration (FNA) technique, which provides an increased amount of cells in the sample and increased ultrasound visibility in comparison with prior art arrangements. Furthermore, the arrangement provides for an effective killing of all lesion cells dislocated in the needle tracts after sampling to prevent local spread (seeding) and also for a way to increases the cell concentration when taking a cell sample from cysts. Moreover, the arrangement provides for methods to distribute the sample droplets on the microscope glass, without significant loss of material.

Finally, the inventive arrangement also relates to a method for taking samples of cells from tumours which brings about the above mentioned advantages.

BACKGROUND ART

Almost all women in the western world will some time during their life be investigated morphologically for breast cancer. There are today two main methods for morphological diagnosis of breast lesions, histopathological examination of surgical or core biopsies and cytopathological examination of fine needle aspirates (FNA).

With cytological diagnosis, single cells and small cell complexes are aspirated from the lesion with the aid of a fine needle in which a lowered air pressure is created during the sampling process. Due to the lower adhesion between tumour cells than between healthy cells, the tumour cell concentration in the sample might be enriched. Subsequent to taking the cell sample, the cell material is examined by e.g. ejecting them onto a glass slide, where they are smeared, fixed, stained and examined cytomorphologically. A final diagnosis can be assessed within 10 min reducing the waiting time and the anxiety for the patient. Ongoing advances in genetics and functional genomics suggest that a completely objective molecular diagnostic procedure in single cells from fine needle aspirates will be available in a near future. Today almost all of the operators are using standard hypodermic needles. The most commonly used needle types have an outer diameter between 0.4 mm and 0.8 mm and a length between 25 mm and 50 mm. Ultrasonic guided FNA needles might be even longer, 80 mm or even more.

The diameter of the core biopsy instruments is several times greater than for the FNA needles, with diameters of up to 3.2 mm. Regarding FNA and core biopsy sampling it is of utmost importance to be aware that increasing diameter of the sampling needle is correlated to increasing risk for complications, especially needle tract seeding, local bleeding and infection. In order to minimise the frequency and extension of complications there is a need to establish routines to achieve final diagnosis with needles of minimal diameters. FNA can be performed with virtually no or minimal side effects. Furthermore, the time consumption for the histopathological procedures is considerably longer compared to cytopathological examination making it hard or impossible to incorporate it in "a one-day diagnostic procedure", which naturally is both economically beneficial and highly demanded from the patients.

However, histopathological examination is able to determine the grade or invasiveness of the tumour, which is not possible using the FNA method. Still the sensitivity and specificity varies greatly with the skill of the aspiration operator and the judging cytologist. If increased sensitivity is reported it is mainly due to a higher degree of sufficient aspirates. In the literature the main reason for choosing core biopsy over FNA is because the frequency of inadequate specimens is lower.

With this in mind it is quite peculiar that standard needles are used for FNA, which are designed for blood sampling or infusion therapy i.e. for quantities of gram when the aspirated sample averages only a few milligrams. Thus, standard needles have large amounts of residual spaces between the Luer coupling and the cannula stainless steel tube, where the sample can stick to the surface and coagulate. The air flow-profile during sample ejection is not well defined and portions of the sample might be sheltered from the air stream during the ejection phase. The needles have residual spaces and registered volumes of more than 70 milligram (of $H_2O$), even when attached to the Record-cone integrated to the syringe. Hence, the compartments are both ill matched in size and configured wrongly to yield optimum amount of sample material. Many experienced FNA-operators are in fact routinely tapping the needle hub against the glass slide to increase the yield. Some even use a small brush to empty the hub from sample. In our studies we have shown that only 25% of the extracted material is obtained on the microscopic glass with a standard 0.6*25 mm needle. The rest is still trapped in the equipment and thrown away after the examination.

If the breast lesions are palpable FNA-sampling is usually performed manually (direct puncture) by the skilled cytological operator, but when lesion size becomes significantly smaller than approx. 10 mm average diameter or are located deeply in the breast, it might be difficult to use the manual puncturing method. Instead ultrasound is nowadays used to guide the needle with high precision. Earlier, stereo-tactic techniques where initially used, but such methods are now used more and more seldom. In the beginning of the ultrasound guided era specially adopted transducers with a guiding needle-channel where often used. However, today a free hand based technique is the most common method. Both the ultrasound transducer and the needle are then held by the operator freely on the non-stabilised breast with the patient lying on her back. This ultrasound guided procedure usually requires a longer needle (up to length 120 mm) and the needle to transducer axis angle becomes quite flat (in the order of 20-30 degrees). The ultrasound frequency commonly used goes from some 3 MHz up to approx. 20 MHz, equivalent to a wavelength-span from 0.5 mm to 0.0745 mm. The $\lambda/4$ figure is of course a critical limit for reflection which here becomes approx. 125 µm to 18.6 µm. Due to the flat angle of reflection at the actual wavelength, the reflection intensity can be quite low which means that it can be difficult to accurately follow the needle-tip approaching the tumour structure during the full procedure. Often the motion of the tissue surrounding the needle tip is used to locate the tip. Several methods have been proposed to enhance the ultrasound visibility, as for instance a plastic cover with trapped miniature air bubbles etc. That method however becomes bulky for the thin needle. It is important to optimise the average angle of incidence and reflection plus establish a significant interface difference in acoustic impedance, for the needle material versus the tissues.

Hence, the inventors in the present application have identified the following problems with the FNA technique as it is used today:
1. The obtained sampling yield is too sparse.
2. The ultrasound visibility is too low.

3. The spread of tumour cells in the needle tract (seeding) occurs.

Another issue to attend is the cell sampling of cysts. If a lesion is cystic, generally several millilitres of fluid are obtained. However, the cell material in the fluid will vary significantly. Presently, the sample may for instance undergo centrifugation subsequent to the sampling procedure in order to retrieve the cells to be examined cytomorphologically. This is a rather labour intensive and time consuming procedure and often the retrieved cell concentration is low. Another method is to put a few droplets of the cystic fluid on the microscopic glass and smear it in the same way as solid cell samples. However, the big drawback with this method is that the number of cells examined is usually too few for a conclusive diagnosis.

Still another issue to attend to is the method used to smear the sample on the microscopic glass. Today the sample is smeared using a second microscopic glass, which generally results in considerable loss of sample material due to wetting of the second glass, which is subsequently dismissed.

Some prior art documents are cited in the following.

WO-96/32146 relates to an aspiration needle and method for use in collecting large cell samples with a source of vacuum for fine needle aspiration cytology without increasing the size of the needle having a rigid elongate tubular member having a distal and proximal extremities. A chamber is formed within the tubular member by a sloping uninterrupted wall leading distally to the opening of the member.

U.S. Pat. No. 5,330,443 relates to an aspiration needle for use with a syringe for fine needle aspiration cytology.

WO-2006/036108 relates to an arrangement for cell sampling using fine needle aspiration technique. A longitudinal movement is applied to the needle when the needle is position inside the tumour, and in addition the arrangement is provided with heat generating means in order to apply a short pulse of heat to the needle in order to lower the risk for the tumour to spread.

WO-2006/036112 relates to an arrangement for therapy of tumours where a needle is intended to be inserted into a tumour and radio frequency energy is intended to be applied between the needle and a ground electrode such that heat is generated in tissue surrounding the needle.

Thus, the object of the present invention is to provide an improved needle arrangement for taking a sample of cells from a lesion with the cytological aspiration technique, which provides increased amount of cells in the sample given a certain needle diameter and increased ultrasound visibility in comparison with prior art arrangements.

Another object of the inventive arrangement is to lower the risk of cancer spread when taking the sample.

DISCLOSURE OF THE INVENTION

The above-identified objects are achieved by an arrangement according to the preambles of the independent claim and provided by the features according to the characteristic portion of the independent claim.

The present inventions also provide for an arrangement that in an effective way increases the cell concentration when taking a cell sample from cystic tumours, which provides for a faster, less labour intensive and representative procedure.

In accordance with a preferred embodiment the arrangement is provided with means to increase the visibility of the needle during insertion when using ultrasound technique.

Moreover, the arrangement provides for methods to smear the sample droplets on the microscope glass, without significant loss of material.

Further embodiments are set forth in the dependent claims.

DETAILED DESCRIPTION OF PREFERRED EMBODIMENTS

Figure 2:
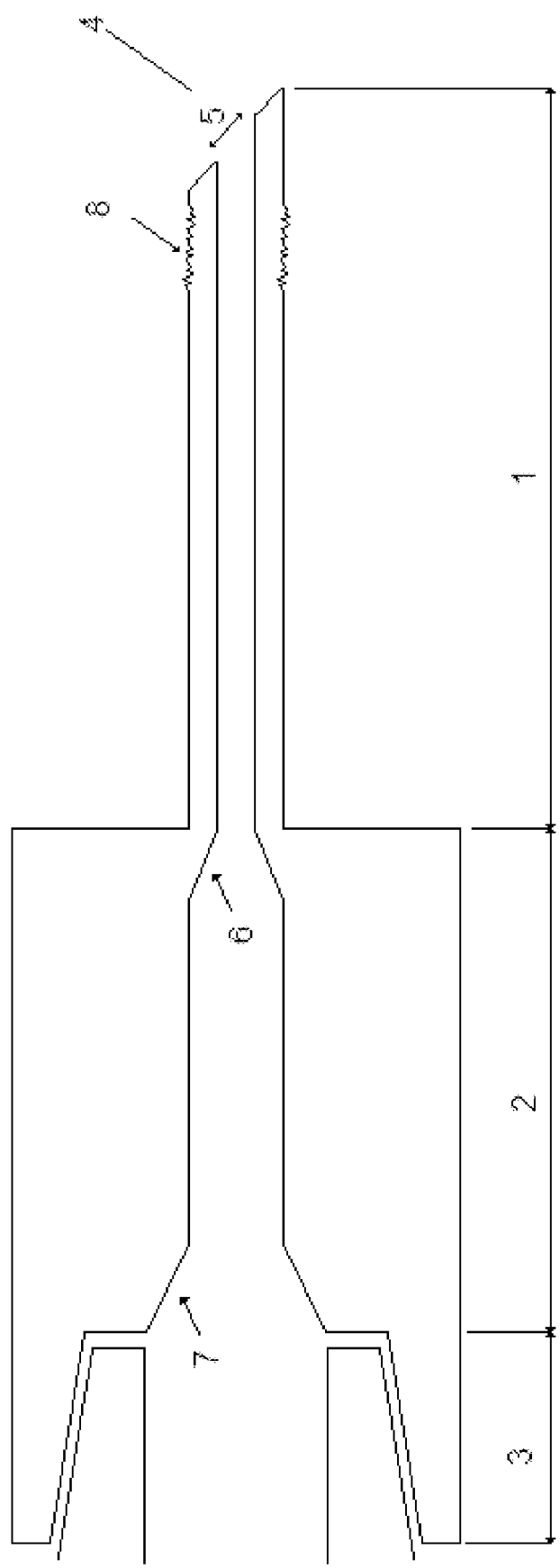
FIG. 2 shows a cross-sectional view of a second embodiment of a fine needle arrangement according to the present invention adapted to ultrasonically guided procedures.
Figure 3:
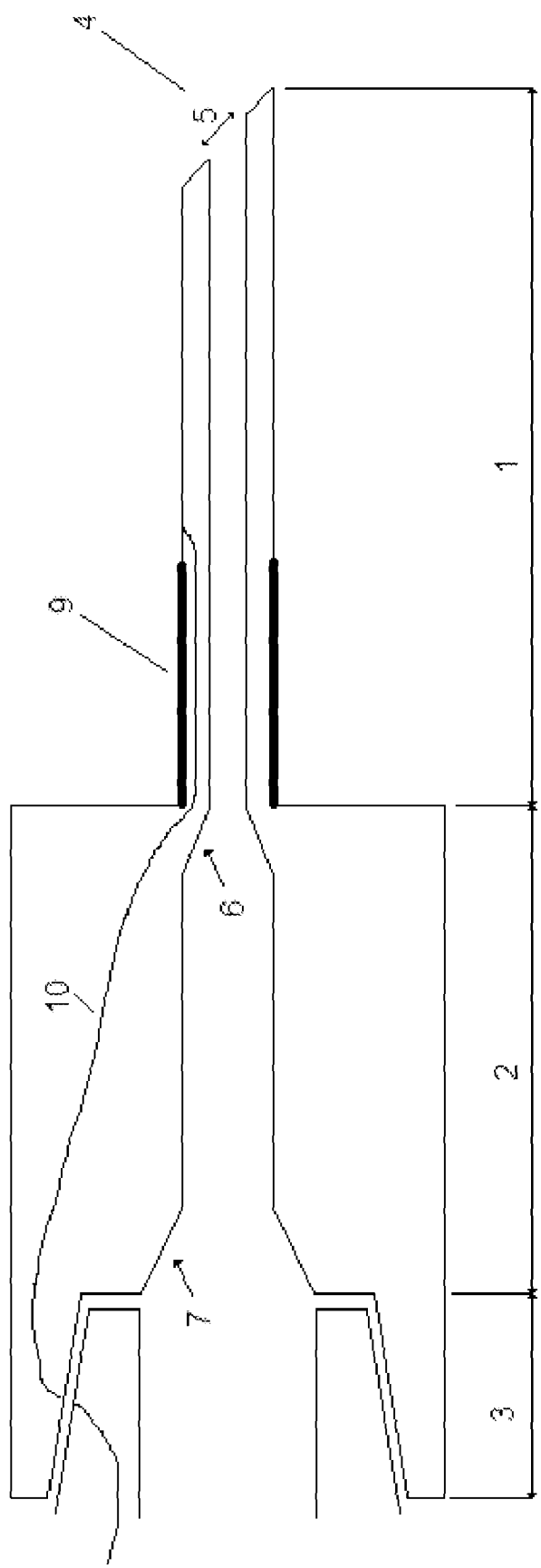
FIG. 3 shows a cross-sectional view of a third embodiment of a fine needle arrangement according to the present invention.
Figure 4:
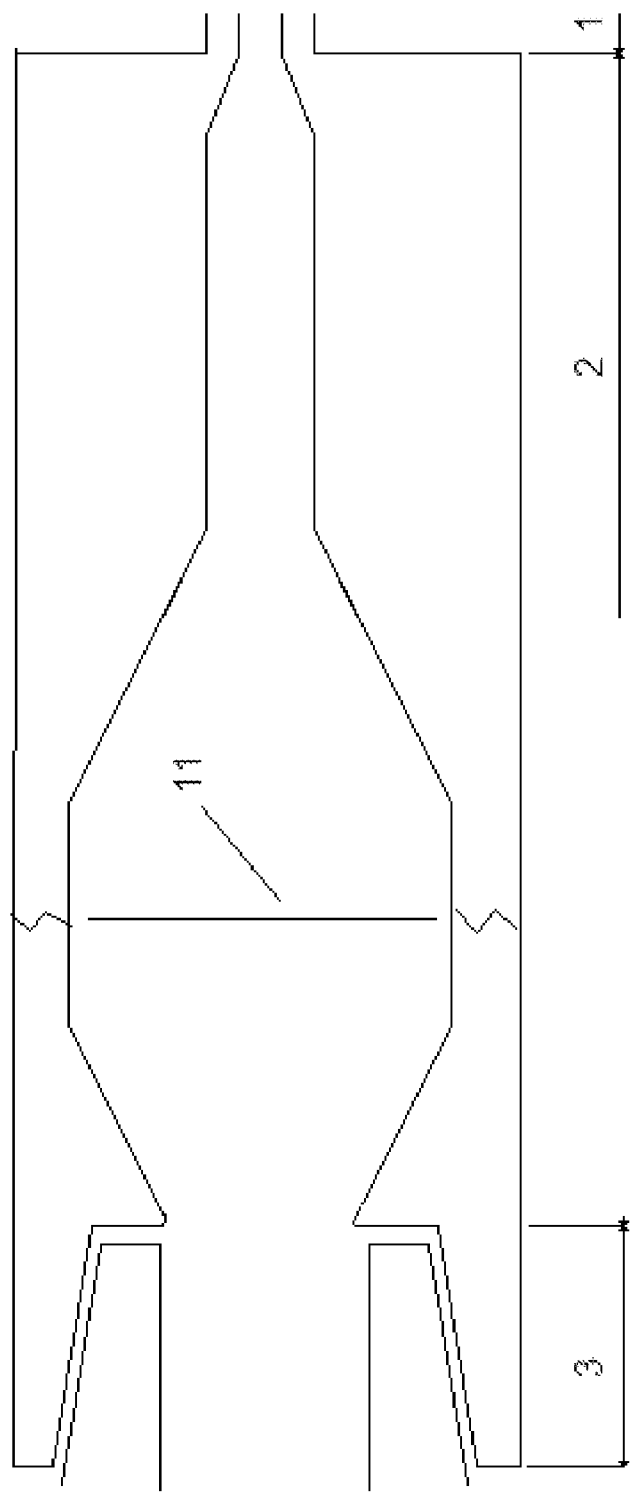
FIG. 4 shows a cross-sectional view of a fourth embodiment of a fine needle arrangement according to the present invention.

With references to the figures, and initially in particular to FIG. 2, a fine needle arrangement for taking a sample of cells from suspicious lesions by using fine needle aspiration (FNA) technique is disclosed. The arrangement comprises a tubular needle member 1, a storage compartment 2 enclosing a chamber, and a coupling 3 to which a connector may be attached.

Figure 1:
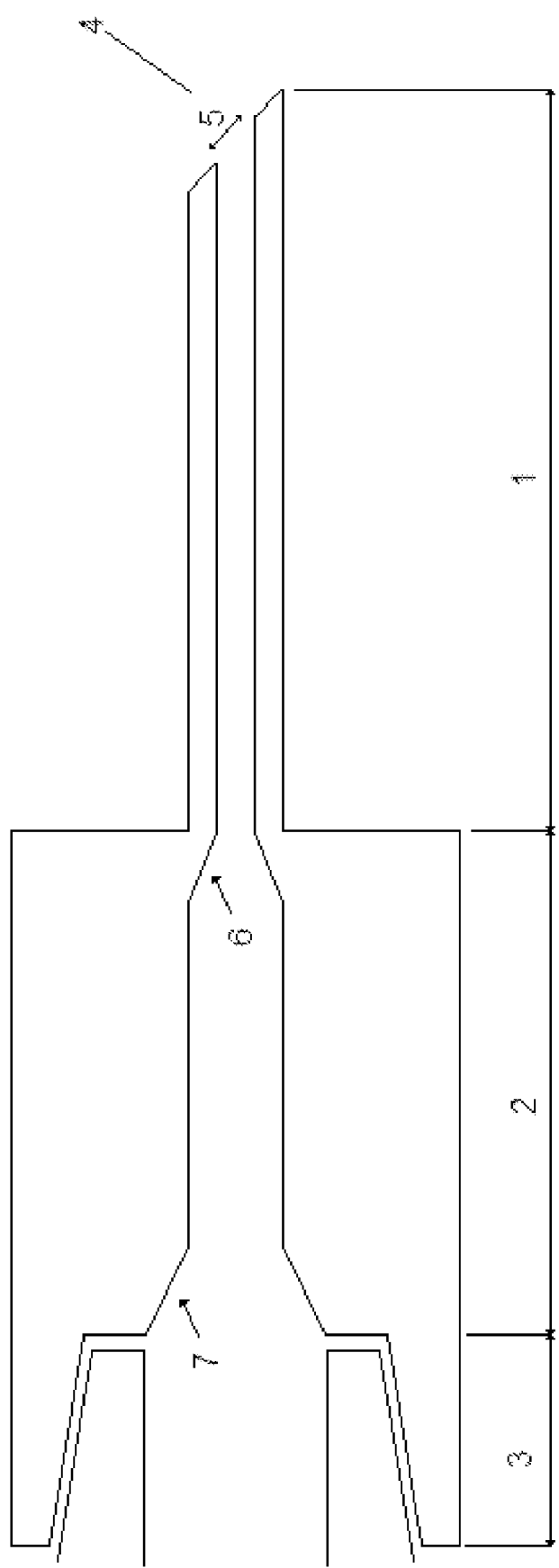
FIG. 1 shows a cross-sectional view of a first embodiment of a fine needle arrangement according to the present invention.
Figure 5:
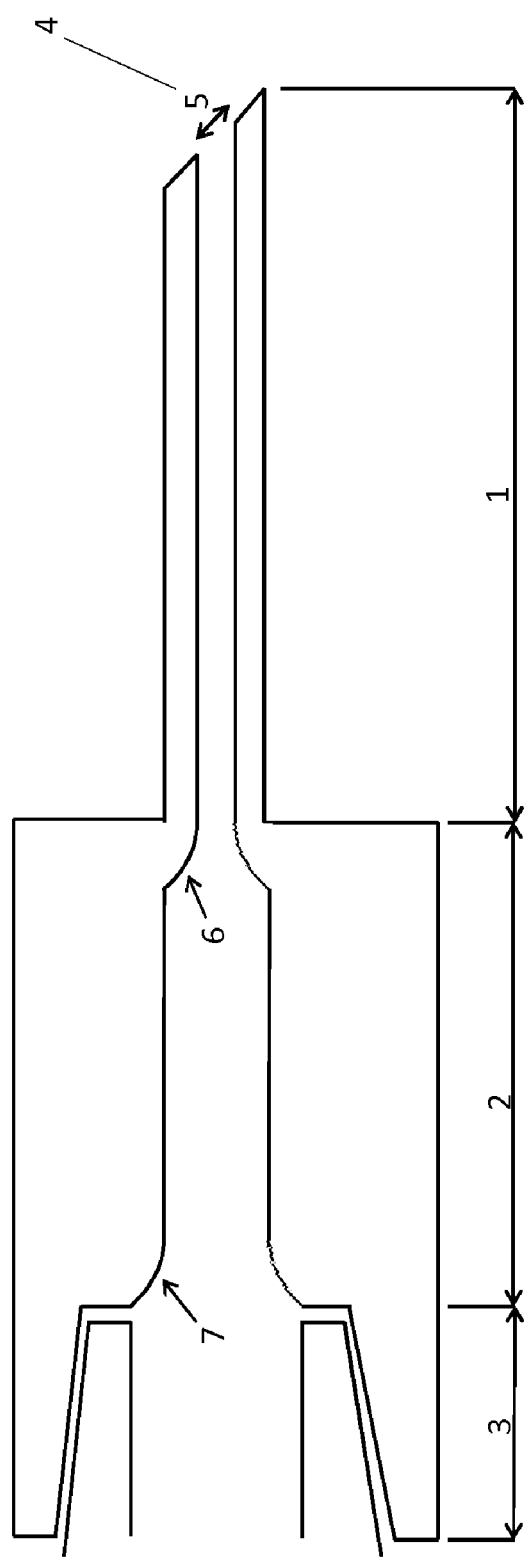
FIG. 5 shows a cross-sectional view of a variation of the first embodiment of a fine needle arrangement according to the present invention.

As may be seen from FIG. 1 the transition between the different parts 1,2 and 3 (6,7) is configured without any residual spaces and with efficient air streaming. These transitions in inner diameter can be of any shape, for example linear (as shown in FIG. 1) or exponential (diagrammatically illustrated in FIG. 5).

Thus, the chamber is configured with a gradually increasing cross-sectional area from the distal part of the chamber to the proximal part of the chamber, such that the chamber has no residual spaces where cell samples may be trapped, and that an efficient air streaming is achieved.

According to a preferred embodiment the chamber has two transition sections, a first transition section 6 where the diameter increases from the inner diameter of the needle to the diameter of the main chamber part, and a second transition section 7 where the diameter increases from the diameter of the main chamber part to the diameter of the connecter to which the arrangement is to be attached.

According to a preferred embodiment the material thickness of the tubular member is decreased, from the distal end and in the proximal direction, which increases the amount of sample yield.

Preferably, and in order to further increase the amount of sample yield the inner surface of the tubular member is polished as to achieve a low frictional surface that then is coated with appropriate material, e.g. PTFE (Teflon), to prevent wetting, i.e. to prevent sample material sticking to the surface.

According to another preferred embodiment of the present invention at least a part 8 of the surface of the needle member has a rougher surface compared to the rest of the needle member surface in order to increase the acoustic reflection of the needle.

This embodiment of the present invention is to adapt the FNA arrangement to ultrasonically guided procedures. By treating at least a short section or part of the needle tube near the tip the surface becomes randomly facetted 8 or roughened, preferably with a precision sandblasting technique or ultrasound cavitation erosion technique, which increases the acoustic reflection of the needle, thus enhancing the visibility of the needle. Preferably, the roughened part defines at least one band running round the needle member. As an alternative, and/or in combination the part may define at least one strip running in the longitudinal direction of the needle member.

A second phenomena that has been identified by the inventors is that this short section of the needle generates an increased local friction over the treated needle-section, without adding much to the overall penetration needle force, which generates a local "tissue movement wave" during penetration—or retraction—that significantly enhances the secondary visibility from the diminutive target propagation movement volume. The diameter of the tubular member, the needle, in this embodiment is preferably 0.6 mm, 0.7 mm or 0.8 with lengths 50 mm and 80 mm. Even longer tubular members can be used in certain difficult cases.

The tubular member has a proximal end connected to the storage compartment 2 and a distal end 4. The configuration and sharpness of the distal end (tip) has major impact on the penetration force and the amount of obtained sample. An increased length of the open section of the tubular member "the cutting length" 5 increases the amount of obtained sample. The configuration of the bevel shape and grinding has great effect on the penetration force.

The tubular member during direct puncturing is preferably 0.5 mm, 0.6 mm or 0.7 mm in diameter with lengths 25 mm and 50 mm and with material thickness in the order of 50 to 200 μm, depending on the length of the needle. Certain stiffness is required in the needle to be able to penetrate the tumour in different directions. The material thickness should be considerable less than present standard needles. For example the inner diameter of a standard 0.6 mm needle are only 0.3 mm.

The length and diameter of the storage compartment (2) must be carefully selected to be able to keep the sample in the needle, and not in the hub or syringe, and finally eject it. If the storage diameter is too large the air-stream speed-profile is too low to successfully eject the sample. Moreover if the length of the compartment is too short sample droplets will be thrust into the hub or syringe, due to the high energy, and be lost. Therefore it is important to arrange the shape so the energy and velocity parameters will be sufficiently distributed along the storage channel. The preferable outline of the compartment for a 0.6*25 mm needle is an inner diameter of 0.7 mm and length 16 mm (6.16 mm$^3$). Depending on the length and the inner diameter of the tubular member this can vary. The general outline of the chamber is preferably about 5-40 mm long and has an inner diameter of approximately 0.5-3 mm. This results in chamber volumes of approximately 1-300 mm$^3$. The storage compartment might also be partly placed within the Luer-coupling and into the Record cone near the plunge lower turning level, in order to prevent adding extra length to the complete needle/syringe system. Moreover it might be fully integrated part of the coupling.

The coupling 3 is connecting the needle and the storage compartment to a male Luer coupling or the like, for example a syringe. The function of the coupling is to connect under pressure to the distal part of the tubular member and to provide a mechanical coupling for successful manoeuvring of the needle during sampling.

The present invention increases the available sample material more than three times compared to the standard needles of the same size. On the other hand a standard 0.7 mm diameter needle extracts more total sample than the present invention of size 0.6 mm. Nevertheless, the available sample on the microscopic glass was similar for both needle types. Additionally, the present invention yielded more total sample for cases with sparse material, which in combination with the better needle efficiency resulted in twice the amount of available material. A high frequency of inadequate specimens only occurs in the cases with the smallest sample volume. Hence, increasing the sampling yield, often in the form of a high content of blood, in the cases with already enough volume adds little to the diagnostic properties of the yield. Thus, our proposed needle keeps the trauma and bleeding to a minimum but still yields more material in the critical cases. Thus, the change in (tip angle) "cutting length" and material thickness increase the number procedures with sufficient extracted total material, whereas the added storage compartment increases the available sample from lesions with sparse total material, such as fibrous tumours, by increasing the efficiency.

Anti-Seeding:

Yet another preferred embodiment of the present invention is to provide any combinations of the above embodiments with anti-seeding properties, which is illustrated in FIG. 3. This feature is further described in the above-mentioned WO-2006/036108 assigned to the applicant of the present application. The anti-seeding is established using a high peak low average radio frequency power burst pulse preferably in a monopole regime, e.g. between the tubular member and the patient body as a bulk. An electric insulation (9) over the tubular member's proximal section is used to prevent the patient skin from the secondary heat pulse. The sample inside the needle is effectively prevented from the generated heat in the tissue by the Faraday's cage effect. Thus, the non-insulated part of the tubular member needs to be connected to an external device preferably via the tubular member and the coupling (10). The anti-seeding pulse will preferably be triggered by changes in circuit impedance. Thus, in order for this to work the insulation must either be:

1. sectioned in two parts (both electrodes for impedance measurements and only the distal part for anti-seeding)
2. slidable (the insulation is fixed on and penetrating the skin)
3. a dielectric coating (impedance is measured in the high frequency range where the impedance over the dielectric coating is small. In the lower frequency range the dielectric coating is an effective insulation)

Increased Concentration of Cells from Liquid Cystic:

To increase the cell concentration in the smear when a sample is to be taken from a cystic lesion, a filter (11), preferably a micro-filter, is incorporated in the needle compartment or provided separately (FIG. 4), which effectively collects the cells of the cystic fluid and thus increases the possibility to enrich the diagnostic cells, e.g. tumour cells. After the fluid has passed the filter, it is removed and the cells are fixed, stained and examined cytomorphologically directly on the filter. This feature is also described in WO-2006/036108. Our experimental work has shown that filters with pore diameters of 10 μm can efficiently accumulate epithelial cells whereas blood cells, e.g. erythrocytes with an average diameter of 7 μm, past the filter. Moreover, we have shown that staining and microscopic examination could be performed on cells located on the filter surface.

Sample Smearing:

In order to prevent sample loss during smearing the second "smearing glass could be exchanged with a low adhesion sterile spatula, which should be provided with the sampling kit. Other alternative embodiments might be automatic non-contact smearing devices using pressurised air streaming or acceleration methods or the like.

Compatibility with our Standardised and Automatic Sampling Equipment:

The present invention may easily be incorporated in the "sampling kit" used in our other inventions described in the above-mentioned WO-2006/036108 and WO-2006/036112.

It will be understood that the invention is not restricted to the above-described exemplifying embodiments thereof and that several conceivable modifications of the invention are possible within the scope of the following claims

The invention claimed is:

1. A fine needle arrangement for taking a sample of cells from suspicious lesions by using fine needle aspiration (FNA) technique, comprising:
    a tubular needle member;
    a storage compartment enclosing a chamber; and
    a coupling to which a connector may be attached,
    wherein said chamber has two transition sections, a first transition section having a diameter that increases continuously from an inner diameter of the needle to a diameter of the main chamber part, and a second transition section having a diameter that increases continuously from the diameter of the main chamber part to an inner diameter of the coupling, and
    wherein said transition sections are configured without any residual spaces, such that the chamber has no residual spaces where cell samples may be trapped, and that an air streaming is achieved.

2. The fine needle arrangement according to claim 1, wherein the diameter increases of the transition sections are linear.

3. The fine needle arrangement according to claim 1, wherein the diameter increases of the transition sections are exponential.

4. The fine needle arrangement according to claim 1, wherein the chamber is about 5-40 mm long and has an inner diameter of approximately 0.5-3 mm.

5. The fine needle arrangement according to claim 1, wherein the inner surface of the chamber is polished as to achieve a low frictional surface that then is covered by a low-frictional coating preventing wetting of the material.

6. The fine needle arrangement according to claim 5, wherein said coating is made from PTFE.

7. The fine needle arrangement according to claim 5, wherein the tubular member is polished as to achieve a low frictional surface that then is covered by a low-frictional coating preventing wetting of the material.

8. The fine needle arrangement according to claim 1, wherein the diameter increases of the first and second transition sections are either of linear or exponential.

* * * * *